US012600661B2

(12) United States Patent
Zeng et al.

(10) Patent No.: US 12,600,661 B2
(45) Date of Patent: Apr. 14, 2026

(54) FIBERGLASS FILTER ELEMENT CONTAINING ZINC OXIDE-BASED COMPOSITE NANOPARTICLES AND METHOD FOR PRODUCING THE SAME

(71) Applicants: Yunnan Huapu quantum Material Co., Ltd, Kunming (CN); ROI Optoelectronics Technology CO, LTD., Shanghai (CN); Chongqing Institute of East China Normal University, Chongqing (CN); East China Normal University, Shanghai (CN)

(72) Inventors: Heping Zeng, Chongqing (CN); Mengyun Hu, Chongqing (CN); Guang Feng, Chongqing (CN)

(73) Assignees: YUNNAN HUAPU QUANTUM MATERIAL CO., LTD, Kunming (CN); ROI OPTOELECTRONICS TECHNOLOGY CO, LTD., Shanghai (CN); CHONGQING INSTITUTE OF EAST CHINA NORMAL UNIVERSITY, Chongqing (CN); EAST CHINA NORMAL UNIVERSITY, Shanghai (CN)

( * ) Notice: Subject to any disclaimer, the term of this patent is extended or adjusted under 35 U.S.C. 154(b) by 1050 days.

(21) Appl. No.: 17/710,397

(22) Filed: Mar. 31, 2022

(65) Prior Publication Data

US 2022/0315476 A1 Oct. 6, 2022

(30) Foreign Application Priority Data

Apr. 2, 2021 (CN) .......................... 202110362528.3
Apr. 2, 2021 (CN) .......................... 202110362680.1

(51) Int. Cl.
  *B01D 39/00* (2006.01)
  *A61L 9/20* (2006.01)
  (Continued)

(52) U.S. Cl.
  CPC .............. *C03C 3/093* (2013.01); *A61L 9/205* (2013.01); *B01D 39/2017* (2013.01); *C03C 13/045* (2013.01)

(58) Field of Classification Search
  CPC ... C03C 3/093; C03C 13/045; C03C 25/1095; C03C 25/1061; A61L 9/205;
  (Continued)

(56) References Cited

FOREIGN PATENT DOCUMENTS

| CN | 112323480 A | * | 2/2021 | ........... D06M 11/44 |
| CN | 112516685 A | | 3/2021 | |

OTHER PUBLICATIONS

Cheng, "Synthesis of hierarchical structure micro/nano oxides and their gas sensing properties," Heilongjiang University Press, Dec. 2013.

(Continued)

*Primary Examiner* — T. Bennett McKenzie
(74) *Attorney, Agent, or Firm* — Hodgson Russ LLP

(57) ABSTRACT

A fiberglass filter element includes: 6 to 12 wt % of zinc oxide-based composite photocatalytic nanoparticles; 3 to 9 wt % of an adhesive system; and 79 to 91 wt % of a superfine fiberglass cotton. The zinc oxide-based composite photocatalytic nanoparticles includes: a rod-like or flower-like zinc oxide photocatalytic nanoparticle (A); a photocatalytic nanoparticle (B), which is one or more selected from graphene, graphene oxide, reduced graphene oxide and graphene quantum dots; a photocatalytic nanoparticle (C), which is one or more selected from a silver nanoparticle and a silver nanowire; and a photocatalytic nanoparticle (D), (Continued)

which is one or more selected from titanium oxide, tin oxide and tungsten oxide.

10 Claims, 4 Drawing Sheets

(51) Int. Cl.
| | | |
|---|---|---|
| *B01D 39/20* | (2006.01) | |
| *C03C 3/093* | (2006.01) | |
| *C03C 13/04* | (2006.01) | |

(58) Field of Classification Search
CPC ........ B01D 39/2017; B01D 2239/0442; B01D 53/885; B01D 2239/0464; B01D 2239/0492; B01D 2239/086; B01D 2239/10; B01D 2239/1225; B01D 2239/1233; B01D 2239/1241; B01D 2257/91; B01D 2258/06; B01D 2259/802; B01D 39/2024; B01D 2239/0258; B01D 2255/104; B01D 2255/20707; B01D 2255/20776; B01D 2255/20792; B01D 2255/2094; B01D 2255/702
USPC ........................................................ 55/527
See application file for complete search history.

(56) References Cited

OTHER PUBLICATIONS

CNIPA, First Office Action for CN Application No. 202110362528.3, May 16, 2022.
CNIPA, First Office Action for CN Application No. 202110362680.1, May 16, 2022.

* cited by examiner

FIBERGLASS FILTER ELEMENT CONTAINING ZINC OXIDE-BASED COMPOSITE NANOPARTICLES AND METHOD FOR PRODUCING THE SAME

CROSS-REFERENCE TO RELATED APPLICATIONS

This application claims priority to and benefits of Chinese Patent Application No. 202110362680.1, and Chinese Patent Application No. 202110362528.3, both filed on Apr. 2, 2021, the entire contents of which are incorporated herein by reference.

FIELD

The present disclosure relates to the field of composite functional materials, and more particularly to a fiberglass filter element containing zinc oxide-based composite nanoparticles and a method for producing the same.

BACKGROUND

Photocatalytic particles have good indoor air purification ability by a photocatalytic mechanism. However, in the related art, the photocatalytic particles prepared by an exiting method are easy to agglomerate, and the photocatalytic particles are commonly mechanically supported on a fiberglass filter element and thus are easy to fall off the filter element, and the commonly used photocatalysts have low utilization efficiency on visible light, all of which lead to reduced photocatalytic antibacterial activity. A common manner to improve the antibacterial effect is to add precious metal antibacterial particles to the filter element, but the cost is high.

SUMMARY

Embodiments of the present disclosure seek to solve at least one of the problems existing in the related art to at least some extent.

According to a first aspect of the present disclosure, a fiberglass filter element is provided. The fiberglass filter element includes: 6 to 12 wt % of zinc oxide-based composite photocatalytic nanoparticles; 3 to 9 wt % of an adhesive system; and 79 to 91 wt % of a superfine fiberglass cotton. The zinc oxide-based composite photocatalytic nanoparticles includes:

a rod-like or flower-like zinc oxide photocatalytic nanoparticle (A);
  a photocatalytic nanoparticle (B), which is one or more selected from graphene, graphene oxide, reduced graphene oxide and graphene quantum dots;
  a photocatalytic nanoparticle (C), which is one or more selected from a silver nanoparticle and a silver nanowire; and
  a photocatalytic nanoparticle (D), which is one or more selected from titanium oxide, tin oxide and tungsten oxide,
  wherein a total amount of the photocatalytic nanoparticles (A), (B), (C) and (D) is 6 to 12%, based on a total weight of the fiberglass filter element.

According to a second aspect of the present disclosure, a method for producing a fiberglass filter element is provided. The method includes:

preparing a zinc ammonia complex precipitate by a reaction between ammonia water and a solution of a zinc source in ultrapure water;
  preparing 4.0 to 8.0 mol/L of a precursor solution of zinc oxide-based composite photocatalytic particles by dispersing the zinc ammonia complex precipitate into 6 mg/mL of a solution comprising photocatalytic nanoparticles (B), (C) and (D) using ammonia water and ultrapure water;
  preparing a uniform pulp by uniformly dispersing two or more kinds of superfine fiberglass cottons with different diameters into the precursor solution by a fiber dissociator;
  processing the pulp into a paper by a paper machine, immersing the paper with an adhesive system, and drying the paper;
  subjecting the paper to a microwave rapid reaction to allow the zinc oxide-based composite photocatalytic nanoparticles to grow in-situ and adhere uniformly on superfine fiberglass to obtain a fiberglass filter paper;
  subjecting the fiberglass filter paper supported with the zinc oxide-based composite photocatalytic nanoparticles to drying and an annealing treatment; and
  pleating the fiberglass filter paper by a pleating machine to obtain the fiberglass filter element.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

Figure 1:
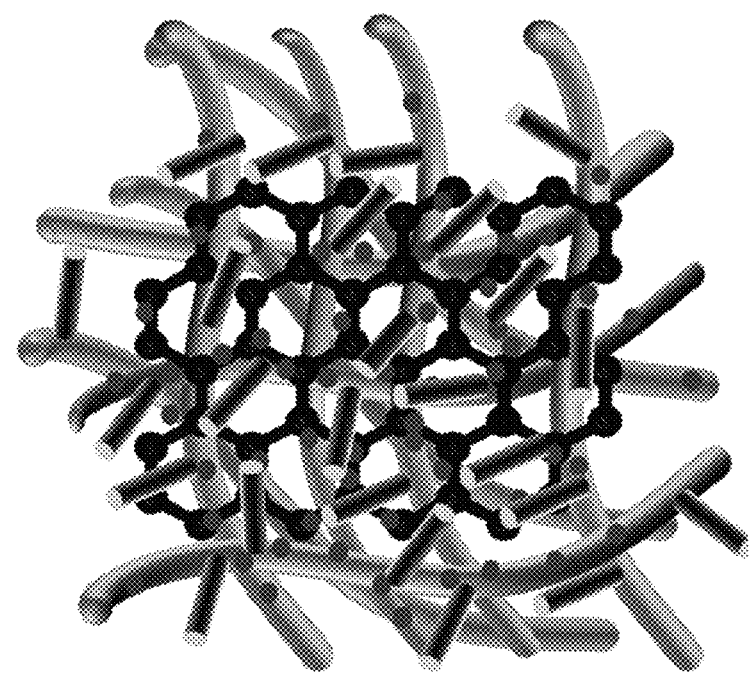
FIG. 1 is a schematic diagram of a fiberglass filter element containing rod-like zinc oxide-based composite photocatalytic nanoparticles according to an embodiment of the present disclosure.
Figure 2:
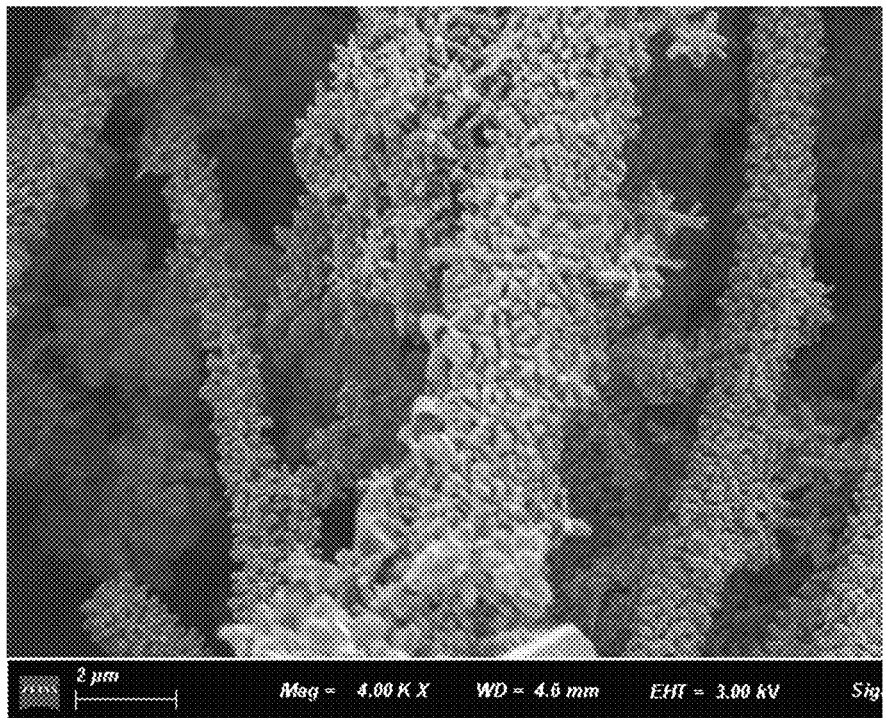
FIG. 2 is a scanning electron microscope (SEM) diagram at 4000× of rod-like zinc oxide-based photocatalytic particles supported on a fiberglass filter element according to an embodiment of the present disclosure.
Figure 3:
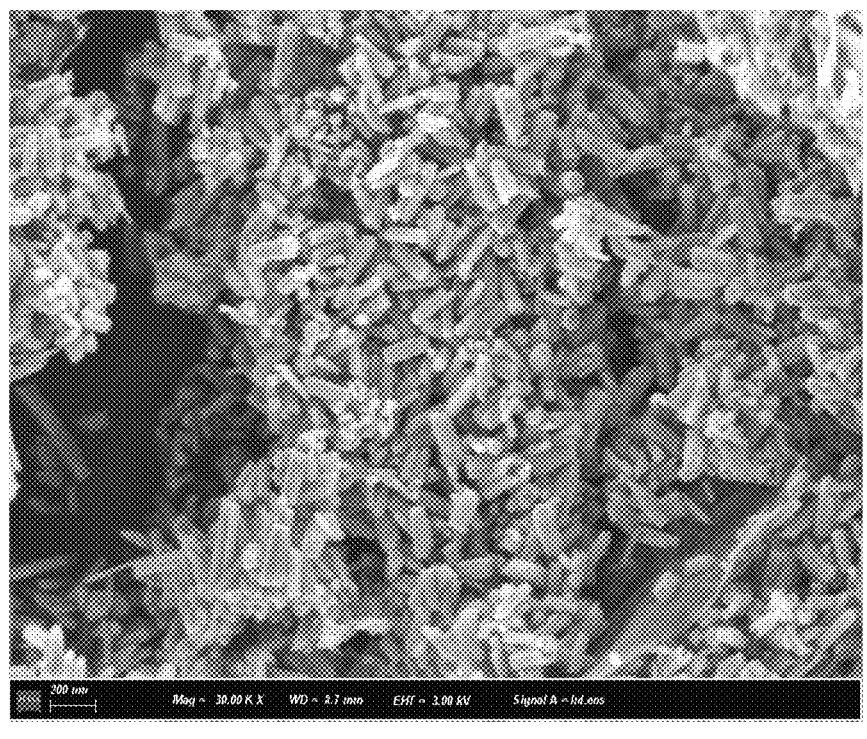
FIG. 3 is a scanning electron microscope (SEM) diagram at 30000× of rod-like zinc oxide-based photocatalytic particles supported on a fiberglass filter element according to an embodiment of the present disclosure.
Figure 4:
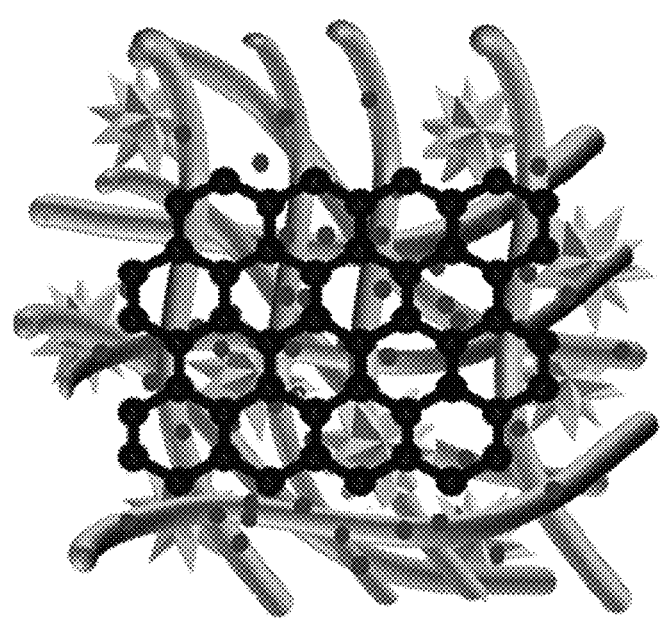
FIG. 4 is a schematic diagram of a fiberglass filter element containing flower-like zinc oxide-based composite photocatalytic nanoparticles according to an embodiment of the present disclosure.
Figure 5:
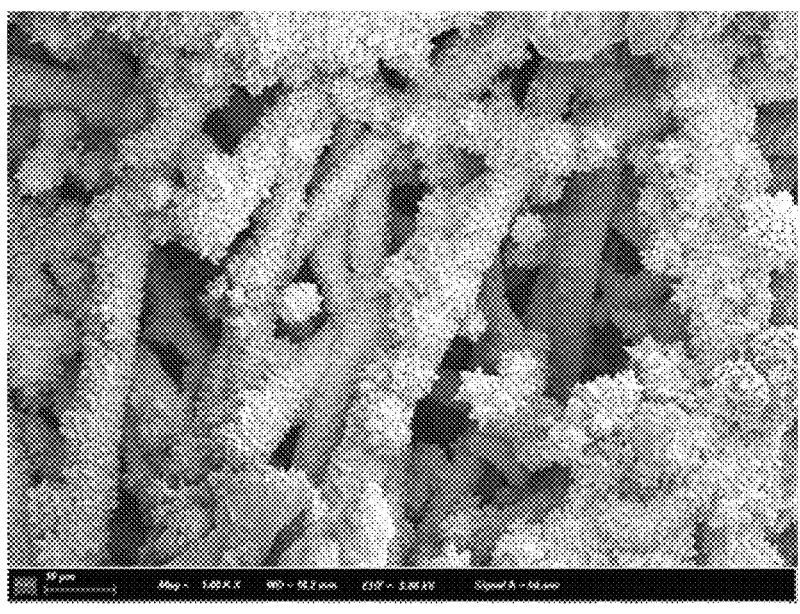
FIG. 5 is a scanning electron microscope (SEM) diagram at 1000× of flower-like zinc oxide-based photocatalytic particles supported on a fiberglass filter element according to an embodiment of the present disclosure.
Figure 6:
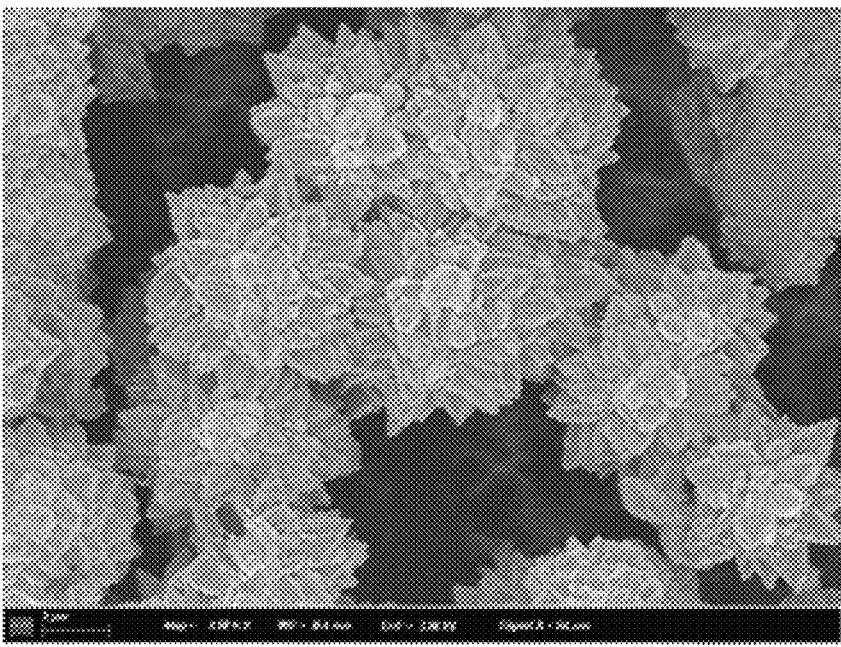
FIG. 6 is a scanning electron microscope (SEM) diagram at 4600× of flower-like zinc oxide-based photocatalytic particles supported on a fiberglass filter element according to an embodiment of the present disclosure.
Figure 7:
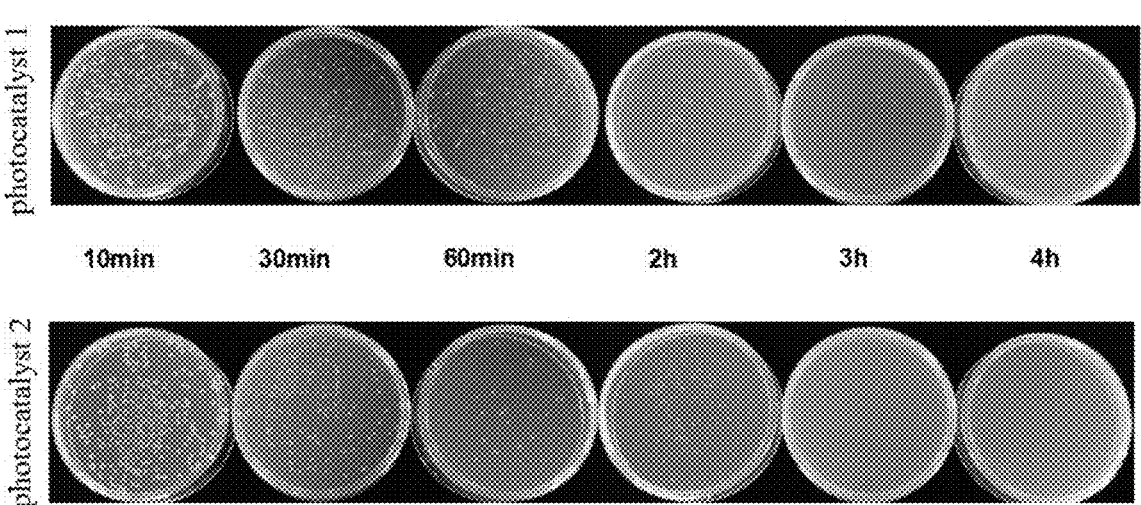
FIG. 7 is a schematic diagram showing antibacterial results under visible light of a fiberglass filter element containing rod-like zinc oxide-based composite photocatalytic nanoparticles according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

According to a first aspect of the present disclosure, a fiberglass filter element is provided. The fiberglass filter element includes: 6 to 12 wt % of zinc oxide-based composite photocatalytic nanoparticles; 3 to 9 wt % of an adhesive system; and 79 to 91 wt % of a superfine fiberglass cotton. The zinc oxide-based composite photocatalytic nanoparticles includes:

a rod-like or flower-like zinc oxide photocatalytic nanoparticle (A);

a photocatalytic nanoparticle (B), which is one or more selected from graphene, graphene oxide, reduced graphene oxide and graphene quantum dots;

a photocatalytic nanoparticle (C), which is one or more selected from a silver nanoparticle and a silver nanowire; and a photocatalytic nanoparticle (D), which is one or more selected from titanium oxide, tin oxide and tungsten oxide, wherein a total amount of the photocatalytic nanoparticles (A), (B), (C) and (D) is 6 to 12%, based on a total weight of the fiberglass filter element.

In an embodiment of the present disclosure, the superfine fiberglass cotton consists of: 56.5 to 66.5 wt % of $SiO_2$; 2.5 to 7.5 wt % of $Al_2O_3$; 4.5 to 8.5 wt % of MgO; 1.5 to 4.5 wt % of CaO; 3 to 6.5 wt % of $B_2O_3$; 4.5 to 7.5 wt % of a combination of $Fe_2O_3$, ZnO and BaO; and 8 to 10.5 wt % of alkali metal oxides $Na_2O$ and $K_2O$.

In an embodiment of the present disclosure, the superfine fiberglass cotton has a fiber diameter normally distributed between 0.6 μm and 4 μm, a mean fiber diameter of 2.2 μm, a fiber length normally distributed between 15 and 30 mm, and a mean fiber length of 20 mm.

In an embodiment of the present disclosure, the superfine fiberglass cotton constitutes a three-dimensional reticular porous structure, and superfine fiberglass with different diameters is interlaced.

In an embodiment of the present disclosure, the adhesive system comprises an adhesive and a modifier.

In an embodiment of the present disclosure, the adhesive system consists of an adhesive and a modifier.

In an embodiment of the present disclosure, the adhesive is one or more selected from a pure acrylic emulsion, a silicone-acrylic emulsion, a styrene-acrylic emulsion, a vinyl acetate-acrylic emulsion, an urea modified phenolic resin, a polyurethane modified phenolic resin, and a melamine modified phenolic resin, and the amount of the adhesive is 2 to 5% based on a total weight of the fiberglass filter element.

In an embodiment of the present disclosure, the modifier is one or more selected from KH550, KH560 and KH792 silane coupling agents, and the amount of the modifier is 1 to 4% based on a total weight of the fiberglass filter element. The modifier may improve the water resistance of the fiberglass filter element and prolong the service life of the fiberglass filter element.

In an embodiment of the present disclosure, the zinc oxide-based composite photocatalytic nanoparticles are uniformly and tightly distributed on superfine fiberglass. The attachment of the zinc oxide-based composite photocatalytic nanoparticles does not change the three-dimensional reticular porous structure of the fiberglass filter element, which makes the fiberglass filter element have good visible light antibacterial performance, while keeping good air filtration performance.

In an embodiment of the present disclosure, the zinc oxide-based composite photocatalytic nanoparticles are introduced into the fiberglass filter element by in situ growth by microwave rapid synthesis.

In an embodiment of the present disclosure, the photocatalytic nanoparticles (B), (C) and (D) are prepared by a microwave synthesis reaction, a precipitation method or a sol-gel method or a hydrothermal method.

According to a second aspect of the present disclosure, there is provided a method for producing a fiberglass filter element as described in any embodiment of the first aspect of the present disclosure. The method includes:

preparing a zinc ammonia complex precipitate by a reaction between ammonia water and a solution of a zinc source in ultrapure water;

preparing 4.0 to 8.0 mol/L of a precursor solution of zinc oxide-based composite photocatalytic particles by dispersing the zinc ammonia complex precipitate into 6 mg/mL of a solution comprising photocatalytic nanoparticles (B), (C) and (D) using ammonia water and ultrapure water;

preparing a uniform pulp by uniformly dispersing two or more kinds of superfine fiberglass cottons with different diameters into the precursor solution by a fiber dissociator;

processing the pulp into a paper by a paper machine, immersing the paper with an adhesive system, and drying the paper;

subjecting the paper to a microwave rapid reaction to allow the zinc oxide-based composite photocatalytic nanoparticles to grow in-situ and adhere uniformly on superfine fiberglass to obtain a fiberglass filter paper;

subjecting the fiberglass filter paper supported with the zinc oxide-based composite photocatalytic nanoparticles to drying and an annealing treatment; and pleating the fiberglass filter paper by a pleating machine to obtain the fiberglass filter element.

In an embodiment of the present disclosure, the zinc ammonia complex precipitate is prepared by: dissolving the zinc source in the ultrapure water, added ammonia water to the solution to control the precipitation of the zinc ammonia complex, subjecting the mixture to extraction filtration to separate the zinc ammonia complex precipitate, washing the zinc ammonia complex precipitate with pure water and anhydrous ethanol, and then drying in a constant temperature drying oven to obtain the dried zinc ammonia complex precipitate.

In an embodiment of the present disclosure, the precursor solution of the zinc oxide-based composite photocatalytic particles is prepared by: adding 6 mg/mL of the solution containing the photocatalytic nanoparticles (B), (C) and (D) into the zinc ammonia complex precipitate and formulating the mixture into a solution of 6 to 8 mol/L using ammonia water and ultrapure water, and subjecting the solution to ultrasonic shake for 30 min to obtain the uniform precursor solution.

In an embodiment of the present disclosure, the superfine fiberglass cottons used in the method have a fiber diameter normally distributed between 0.6 μm and 4 μm and a mean fiber diameter of 2.2 μm, and the superfine fiberglass cotton is of a fiber length normally distributed between 15 and 30 mm and a mean fiber length of 20 mm.

In an embodiment of the present disclosure, the zinc source is one or more selected from zinc stearate, zinc nitrate hexahydrate, zinc laurate, zinc acetate, zinc carbonate, and zinc sulfate.

In an embodiment of the present disclosure, the photocatalytic nanoparticle (B) is one or more selected from graphene, graphene oxide, reduced graphene oxide and graphene quantum dots, and the photocatalytic nanoparticle (B) has a diameter ranging from 30 to 50 nm, and a content of the photocatalytic nanoparticle (B) is 1 to 4% relative to a total weight of the fiberglass filter element. In the method according to embodiments of the present disclosure, the two or more kinds of superfine fiberglass cottons are able to adsorb the defined amount of graphene, and the presence of graphene can not only effectively avoid the agglomeration of zinc oxide to make the zinc oxide uniformly supported on the superfine fiberglass, but also provide more growth sites.

In an embodiment of the present disclosure, the photocatalytic nanoparticle (C) is one or more selected from a silver nanoparticle and a silver nanowire, the photocatalytic nanoparticle (C) has a diameter ranging from 20 to 30 nm, and a content of the photocatalytic nanoparticle (C) is 1 to 4% relative to a total weight of the fiberglass filter element. In the method according to embodiments of the present disclosure, the two or more kinds of superfine fiberglass cottons are able to adsorb the defined amount of the photocatalytic nanoparticle (C) to adjust the response to the visible light, and increase the adsorption characteristics and specific surface area of the filter element.

In an embodiment of the present disclosure, the photocatalytic nanoparticle (D) is one or more selected from titanium oxide, tin oxide and tungsten oxide, the photocatalytic nanoparticle (D) has a length ranging from 120 to 250 nm, and a content of the photocatalytic nanoparticle (D) is 2 to 4% relative to a total weight of the fiberglass filter element. In the method according to embodiments of the present disclosure, the two or more kinds of superfine fiberglass cottons are able to adsorb the defined amount of the photocatalytic nanoparticle (D) to adjust the adsorption characteristics and increase photocatalytic activity.

In an embodiment of the present disclosure, the preparing the uniform pulp by uniformly dispersing two or more kinds of superfine fiberglass cottons with different diameters into the precursor solution by the fiber dissociator includes: dispersing the two or more kinds of superfine fiberglass cottons with different diameters into the precursor solution by the fiber dissociator at a rotating speed of 5000 to 12000 r/min. The pulp has a concentration of 5 to 10 wt % and a pH of 3.0 to 5.0.

In an embodiment of the present disclosure, drying the paper includes: drying the paper at a drying plate at a temperature ranging from 100 to 115° C. for 4 to 6 min.

In an embodiment of the present disclosure, the annealing treatment is performed at a temperature ranging from 60 to 100° C. for 30 to 60 min.

In an embodiment of the present disclosure, the precursor solution has a concentration of 6.0 to 8.0 mol/L, and the microwave rapid reaction is performed at a temperature ranging from 100 to 200° C. for 6 to 12 min. A zinc oxide photocatalytic particle formed in the method and contained in the zinc oxide-based composite photocatalytic nanoparticles is rod-like, and has a length ranging from 100 to 200 nm and a diameter ranging from 50 to 100 nm, and a content of the zinc oxide photocatalytic particle is 2 to 6%, relative to a total weight of the fiberglass filter element.

In an embodiment of the present disclosure, the precursor solution has a concentration of 4.0 to 5.0 mol/L, and the microwave rapid reaction is performed at a temperature ranging from 70 to 100° C. for 1 to 4 min. A zinc oxide photocatalytic particle formed in the method and contained in the zinc oxide-based composite photocatalytic nanoparticles is flower-like, and has a diameter ranging from 2 to 4 μm, and a content of the zinc oxide photocatalytic particle is 2 to 6%, relative to a total weight of the fiberglass filter element.

Similar to the zinc oxide-based composite photocatalytic nanoparticles, the method of the present disclosure is also applicable to produce the silicon oxide-based composite photocatalytic nanoparticles or zirconium oxide-based composite photocatalytic nanoparticles as well as a fiberglass filter element having the same.

Embodiments of the present disclosure have the following technical advantageous.

In embodiments of the present disclosure, composite photocatalytic nanoparticles are supported first on the superfine fiberglass cotton as a seed layer, which provides growth sites for the subsequent growth of the rod-like or flower-like zinc oxide, which greatly increases the binding force of the zinc oxide-based composite photocatalytic nanoparticles. At the same time, the zinc oxide-based composite photocatalytic nanoparticles are better distributed and coated on each superfine fiberglass, the nanoparticles are not prone to agglomeration, so that the finally produced air purification fiberglass filter element has excellent photocatalytic antibacterial properties.

In embodiments of the present disclosure, the rod-like or flower-like zinc oxide-based composite photocatalytic nanoparticles are synthesized in-suit on the superfine fiberglass by the microwave rapid reaction. Compared with traditional photocatalytic particles, other types of photocatalytic nanoparticles used in the present disclosure are uniformly distributed and coated on the rod-like or flower-like zinc oxide photocatalytic nanoparticles, and the rod-like or flower-like zinc oxide photocatalytic nanoparticles have a larger specific surface area and thus provide more active sites, which effectively improve the antibacterial and bactericidal effects of the finally produced air purification fiberglass filter element. In particular, the air purification fiberglass filter element produced according to embodiments of the present disclosure can realize photocatalytic antibacterial inactivation on *Escherichia coli* and *Staphylococcus aureus* under the visible light within a short time.

By using the precursor mixture of the zinc oxide-based composite photocatalytic particles, food-grade zinc oxide is introduced into the fiberglass filter element, which does not cause rejection reaction of human body and thus avoids the harm of the photocatalyst to human body, and at the same time, other modified particles like graphene which can be grown in large quantities are introduced into the fiberglass filter element, which not only improve the dispersion degree of photocatalytic particles, but also significantly improve the visible light photocatalytic antibacterial performance.

In addition, the flower-like zinc oxide photocatalytic nanoparticles obtained according to embodiments of the present disclosure can provide diverse supporting directions and active sites, so that under the same loading amount of photocatalytic particles, the fiberglass filter element containing flower-like zinc oxide-based composite photocatalytic nanoparticles achieve higher degradation and bactericidal properties under visible light.

In the following, the method for producing the fiberglass filter element according to embodiments of the present disclosure will be described in detail referring to the following examples.

Example 1

A solution of 2 g zinc acetate in 50 ml deionized water was add with 1.5 ml ammonia water, resulting in precipitation of zinc ammonia complex, and then the mixture was subjected to extraction filtration, and the obtained zinc ammonia complex was dried in an oven at 45° C. for 10 h. 6 mol/L zinc oxide precursor solution was prepared from the zinc ammonia complex, silver nanowire, graphene oxide and nano-$TiO_2$ using 20 ml ammonia water and 20 ml deionized water. 40 weight parts of superfine fiberglass cotton with a diameter of 3.0 μm and 10 weight parts of superfine fiberglass cotton with a diameter of 1.0 μm were dispersed into the zinc oxide precursor solution by a fiber dissociator at a speed of 6000 r/min for 3 min to obtain a pulp suspension of 6% by weight. The pulp suspension was transported by a slurry conveyor to a paper machine, where the pulp suspension was wet formed into papers. Then, the formed wet paper was immersed by an adhesive system containing polyurethane modified phenolic resin and KH550 in such a way that the amount of the adhesive system contained in the finally obtained fiberglass filter element is 3 wt % based on the total weight of the finally obtained fiberglass filter element, and then dried on a drying plate at 100° C. for 5 min to obtain a filter paper. Subsequently, the filter paper was put into a microwave rapid reactor at 100° C. for 6 min, and then dried in a blast air oven at 60° C. for 30 min to obtain a fiberglass filter paper. Afterwards, the fiberglass filter paper was pleated by a pleating machine to finally obtain an air purification fiberglass filter element. The air purification fiberglass filter element obtained thereby contains rod-like zinc oxide-based composite nanoparticles, can achieve 100% inactivation on *Escherichia coli* under visible light for 5 h, and have a filtration resistance of 480 Pa, a filtration efficiency of 99.999%, and a strength of 0.9 KN/m.

Example 2

A solution of 3 g zinc sulfate in 50 ml deionized water was add with 2 ml ammonia water, resulting in precipitation of zinc ammonia complex, and then the mixture was subjected to extraction filtration, and the obtained zinc ammonia complex was dried in an oven at 45° C. for 10 h. 7 mol/L zinc oxide precursor solution was prepared from the zinc ammonia complex, silver nanowire, graphene oxide and nano-$TiO_2$ using 20 ml ammonia water and 20 ml deionized water. 40 weight parts of superfine fiberglass cotton with a diameter of 3.5 μm and 10 weight parts of superfine fiberglass cotton with a diameter of 1.5 μm were dispersed into the zinc oxide precursor solution by a fiber dissociator at a speed of 7000 r/min for 4 min to obtain a pulp suspension of 7% by weight. The pulp suspension was transported by a slurry conveyor to a paper machine, where the pulp suspension was wet formed into papers. Then, the formed wet paper was immersed by an adhesive system containing polyurethane modified phenolic resin and KH550 in such a way that the amount of the adhesive system contained in the finally obtained fiberglass filter element is 6 wt % based on the total weight of the finally obtained fiberglass filter element, and then dried on a drying plate at 100° C. for 5 min to obtain a filter paper. Subsequently, the filter paper was put into a microwave rapid reactor at 150° C. for 8 min, and then dried in a blast air oven at 60° C. for 30 min to obtain a fiberglass filter paper. Afterwards, the fiberglass filter paper was pleated by a pleating machine to finally obtain an air purification fiberglass filter element. The air purification fiberglass filter element obtained thereby contains rod-like zinc oxide-based composite nanoparticles, can achieve 100% inactivation on *Escherichia coli* under visible light for 4 h, and have a filtration resistance of 480 Pa, a filtration efficiency of 99.999%, and a strength of 0.9 KN/m.

Example 3

A solution of 4 g zinc acetate in 50 ml deionized water was add with 3 ml ammonia water, resulting in precipitation of zinc ammonia complex, and then the mixture was subjected to extraction filtration, and the obtained zinc ammonia complex was dried in an oven at 45° C. for 10 h. 8 mol/L zinc oxide precursor solution was prepared from the zinc ammonia complex, silver nanoparticles, graphene oxide and nano-$TiO_2$ using 20 ml ammonia water and 20 ml deionized water. 40 weight parts of superfine fiberglass cotton with a diameter of 3.5 μm and 10 weight parts of superfine fiberglass cotton with a diameter of 1.5 μm were dispersed into the zinc oxide precursor solution by a fiber dissociator at a speed of 8000 r/min for 4 min to obtain a pulp suspension of 9% by weight. The pulp suspension was transported by a slurry conveyor to a paper machine, where the pulp suspension was wet formed into papers. Then, the formed wet paper was immersed by an adhesive system containing polyurethane modified phenolic resin and KH550 in such a way that the amount of the adhesive system contained in the finally obtained fiberglass filter element is 6 wt % based on the total weight of the finally obtained fiberglass filter element, and then dried on a drying plate at 100° C. for 5 min to obtain a filter paper. Subsequently, the filter paper was put into a microwave rapid reactor at 200° C. for 12 min, and then dried in a blast air oven at 60° C. for 30 min to obtain a fiberglass filter paper. Afterwards, the fiberglass filter paper was pleated by a pleating machine to finally obtain an air purification fiberglass filter element. The air purification fiberglass filter element obtained thereby contains rod-like zinc oxide-based composite nanoparticles, can achieve 100% inactivation on *Escherichia coli* under visible light for 3 h, and have a filtration resistance of 480 Pa, a filtration efficiency of 99.999%, and a strength of 0.9 KN/m.

Example 4

A solution of 2 g zinc acetate in 50 ml deionized water was add with 1.5 ml ammonia water, resulting in precipitation of zinc ammonia complex, and then the mixture was subjected to extraction filtration, and the obtained zinc ammonia complex was dried in an oven at 45° C. for 10 h. 4 mol/L zinc oxide precursor solution was prepared from the zinc ammonia complex, 250 nm $TiO_2$ particles, 20 nm silver nanoparticles, graphene quantum dots and nano-tungsten oxide using 20 ml ammonia water and 20 ml deionized water. 40 weight parts of superfine fiberglass cotton with a diameter of 3.0 μm and 10 weight parts of superfine fiberglass cotton with a diameter of 0.6 μm were immersed in the zinc oxide precursor solution for 5 min, and then dispersed into the zinc oxide precursor solution by a fiber dissociator at a speed of 6000 r/min for 3 min to obtain a pulp suspension of 6% by weight. The pulp suspension was transported by a slurry conveyor to a paper machine, where the pulp suspension was wet formed into papers. Then, the formed wet paper was immersed by an adhesive system containing polyurethane modified phenolic resin and KH550 in such a way that the amount of the adhesive system contained in the finally obtained fiberglass filter element is 3 wt % based on the total weight of the finally obtained fiberglass filter element, and then dried on a drying plate at 100° C. for 5 min to obtain a filter paper. Subsequently, the filter paper was put into a microwave rapid reactor at 70° C. for 1 min, and then dried in a blast air oven at 60° C. for 30 min to obtain a fiberglass filter paper. Afterwards, the fiberglass filter paper was pleated by a pleating machine to finally obtain an air purification fiberglass filter element. The air purification fiberglass filter element obtained thereby contains flower-like zinc oxide-based composite nanoparticles, can achieve 100% inactivation on *Escherichia coli* under visible light for 4 h, and have a filtration resistance of 480 Pa, a filtration efficiency of 99.999%, and a strength of 0.9 KN/m.

Example 5

A solution of 2 g zinc sulfate in 50 ml deionized water was add with 1.5 ml ammonia water, resulting in precipitation of zinc ammonia complex, and then the mixture was subjected to extraction filtration, and the obtained zinc ammonia complex was dried in an oven at 45° C. for 10 h. 5 mol/L zinc oxide precursor solution was prepared from the zinc ammonia complex, silver nanowires, grapheme, nano-tungsten oxide, 200 nm $TiO_2$ particles and 20 nm silver nanoparticles using 20 ml ammonia water and 20 ml deionized water. 40 weight parts of superfine fiberglass cotton with a diameter of 3.0 μm and 10 weight parts of superfine fiberglass cotton with a diameter of 0.6 μm were immersed in the zinc oxide precursor solution for 5 min, and then dispersed into the zinc oxide precursor solution by a fiber dissociator at a speed of 7000 r/min for 4 min to obtain a pulp suspension of 7% by weight. The pulp suspension was transported by a slurry conveyor to a paper machine, where the pulp suspension was wet formed into papers. Then, the formed wet paper was immersed by an adhesive system containing polyurethane modified phenolic resin and KH550 in such a way that the amount of the adhesive system contained in the finally obtained fiberglass filter element is 6 wt % based on the total weight of the finally obtained fiberglass filter element, and then dried on a drying plate at 100° C. for 5 min to obtain a filter paper. Subsequently, the filter paper was put into a microwave rapid reactor at 85° C. for 2 min, and then dried in a blast air oven at 60° C. for 30 min to obtain a fiberglass filter paper. Afterwards, the fiberglass filter paper was pleated by a pleating machine to finally obtain an air purification fiberglass filter element. The air purification fiberglass filter element obtained thereby contains flower-like zinc oxide-based composite nanoparticles, can achieve 100% inactivation on *Escherichia coli* under visible light for 3 h, and have a filtration resistance of 480 Pa, a filtration efficiency of 99.999%, and a strength of 0.9 KN/m.

Example 6

A solution of 4 g zinc sulfate in 50 ml deionized water was add with 3 ml ammonia water, resulting in precipitation of zinc ammonia complex, and then the mixture was subjected to extraction filtration, and the obtained zinc ammonia complex was dried in an oven at 45° C. for 10 h. 6 mol/L zinc oxide precursor solution was prepared from the zinc ammonia complex, silver nanowires, grapheme, nano-tungsten oxide, 120 nm $TiO_2$ particles and 20 nm silver nanoparticles using 20 ml ammonia water and 20 ml deionized water. 40 weight parts of superfine fiberglass cotton with a diameter of 3.5 μm and 10 weight parts of superfine fiberglass cotton with a diameter of 0.6 μm were immersed in the zinc oxide precursor solution for 5 min, and then dispersed into the zinc oxide precursor solution by a fiber dissociator at a speed of 8000 r/min for 4 min to obtain a pulp suspension of 10% by weight. The pulp suspension was transported by a slurry conveyor to a paper machine, where the pulp suspension was wet formed into papers. Then, the formed wet paper was immersed by an adhesive system containing polyurethane modified phenolic resin and KH550 in such a way that the amount of the adhesive system contained in the finally obtained fiberglass filter element is 9 wt % based on the total weight of the finally obtained fiberglass filter element, and then dried on a drying plate at 100° C. for 5 min to obtain a filter paper. Subsequently, the filter paper was put into a microwave rapid reactor at 100° C. for 5 min, and then dried in a blast air oven at 60° C. for 30 min to obtain a fiberglass filter paper. Afterwards, the fiberglass filter paper was pleated by a pleating machine to finally obtain an air purification fiberglass filter element. The air purification fiberglass filter element obtained thereby contains flower-like zinc oxide-based composite nanoparticles, can achieve 100% inactivation on *Escherichia coli* under visible light for 2 h, and have a filtration resistance of 480 Pa, a filtration efficiency of 99.999%, and a strength of 0.9 KN/m.

Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, in the absence of contradiction, those skilled in the art can combine the different embodiments or examples described in this specification, or combine the features of different embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for producing a fiberglass filter element, comprising:

preparing a zinc ammonia complex precipitate by a reaction between ammonia water and a solution of a zinc source in ultrapure water;

preparing 4.0 to 8.0 mol/L of a precursor solution of zinc oxide-based composite photocatalytic nanoparticles by dispersing the zinc ammonia complex precipitate into 6 mg/mL of a solution comprising photocatalytic nanoparticles (B), (C) and (D) using ammonia water and ultrapure water;

preparing a uniform pulp by uniformly dispersing two or more kinds of superfine fiberglass cottons with different diameters into the precursor solution by a fiber dissociator;

processing the pulp into a paper by a paper machine, immersing the paper with an adhesive system, and drying the paper;

subjecting the paper to a microwave reaction to allow the zinc oxide-based composite photocatalytic nanoparticles to grow in-situ and adhere uniformly on superfine fiberglass to obtain a fiberglass filter paper;

subjecting the fiberglass filter paper supported with the zinc oxide-based composite photocatalytic nanoparticles to drying and an annealing treatment; and pleating the fiberglass filter paper by a pleating machine to obtain the fiberglass filter element.

2. The method according to claim 1, wherein the zinc source is one or more selected from zinc stearate, zinc nitrate hexahydrate, zinc laurate, zinc acetate, zinc carbonate, and zinc sulfate.

3. The method according to claim 1, wherein the photocatalytic nanoparticle (B) is one or more selected from graphene, graphene oxide, reduced graphene oxide and graphene quantum dots, and the photocatalytic nanoparticle (B) has a diameter ranging from 30 to 50 nm, and a content of the photocatalytic nanoparticle (B) is 1 to 4% relative to a total weight of the fiberglass filter element.

4. The method according to claim 1, wherein the photocatalytic nanoparticle (C) is one or more selected from a silver nanoparticle and a silver nanowire, the photocatalytic nanoparticle (C) has a diameter ranging from 20 to 30 nm, and a content of the photocatalytic nanoparticle (C) is 1 to 4% relative to a total weight of the fiberglass filter element.

5. The method according to claim 1, wherein the photocatalytic nanoparticle (D) is one or more selected from titanium oxide, tin oxide and tungsten oxide, the photocatalytic nanoparticle (D) has a length ranging from 120 to 250 nm, and a content of the photocatalytic nanoparticle (D) is 2 to 4% relative to a total weight of the fiberglass filter element.

6. The method according to claim 1, wherein preparing the uniform pulp by uniformly dispersing two or more kinds of superfine fiberglass cottons with different diameters into the precursor solution by the fiber dissociator comprises:

dispersing the two or more kinds of superfine fiberglass cottons with different diameters into the precursor solution by the fiber dissociator at a rotating speed of 5000 to 12000 r/min, wherein the pulp has a concentration of 5 to 10 wt % and a pH of 3.0 to 5.0.

7. The method according to claim 1, wherein drying the paper comprises:

drying the paper at a drying plate at a temperature ranging from 100 to 115° C. for 4 to 6 min.

8. The method according to claim 1, wherein the annealing treatment is performed at a temperature ranging from 60 to 100° C. for 30 to 60 min.

9. The method according to claim 1, wherein the precursor solution has a concentration of 6.0 to 8.0 mol/L, and the microwave reaction is performed at a temperature ranging from 100 to 200° C. for 6 to 12 min;

wherein a zinc oxide photocatalytic particle formed in the method and contained in the zinc oxide-based composite photocatalytic nanoparticles is a rod, and has a length ranging from 100 to 200 nm and a diameter ranging from 50 to 100 nm, and a content of the zinc oxide photocatalytic particle is 2 to 6%, relative to a total weight of the fiberglass filter element.

10. The method according to claim 1, wherein the precursor solution has a concentration of 4.0 to 5.0 mol/L, and the microwave rapid reaction is performed at a temperature ranging from 70 to 100° C. for 1 to 4 min, wherein a zinc oxide photocatalytic particle formed in the method and contained in the zinc oxide-based composite photocatalytic nanoparticles is shaped as a flower, and has a diameter ranging from 2 to 4 μm, and a content of the zinc oxide photocatalytic particle is 2 to 6%, relative to a total weight of the fiberglass filter element.

* * * * *